United States Patent [19]

Huffman

[11] 4,301,357
[45] Nov. 17, 1981

[54] ELECTRICALLY HEATED WAX SPATULA USING A DIODE AS THE HEATING ELEMENT

[75] Inventor: Ronald E. Huffman, Tucson, Ariz.

[73] Assignee: KV33 Corporation, Tucson, Ariz.

[21] Appl. No.: 68,932

[22] Filed: Aug. 23, 1979

[51] Int. Cl.³ .................. H05B 1/00; A61C 13/20; B23K 3/04
[52] U.S. Cl. .................................. 219/229; 165/185; 219/239; 219/240; 219/501; 219/541; 433/32
[58] Field of Search .................. 219/221, 227–230, 219/236–242, 501, 209, 210, 541; 165/185; 433/32

[56] References Cited

U.S. PATENT DOCUMENTS

| | | | |
|---|---|---|---|
| 2,725,505 | 11/1955 | Webster et al. | 165/185 X |
| 2,887,628 | 5/1959 | Zierdt | 165/185 |
| 3,178,556 | 4/1965 | Cornwall et al. | 219/242 X |
| 3,333,086 | 7/1967 | Williams | 219/501 |
| 3,358,152 | 12/1967 | Alexakis | 219/501 X |
| 3,782,366 | 1/1974 | Brown | 219/240 X |
| 3,902,043 | 8/1975 | Rogan | 219/242 |

FOREIGN PATENT DOCUMENTS 2150585 5/1972 Fed. Rep. of Germany ...... 219/241

Primary Examiner—A. Bartis
Attorney, Agent, or Firm—Cahill, Sutton & Thomas

[57] ABSTRACT

An electrically heated spatula for working heat softenable materials, such as dental wax, includes an elongated hollow sleeve secured at one end to a handle and having a heat producing diode unit supported at the other end. The diode unit includes a hollow metallic cylinder with an apertured metallic end wall. A forward biased diode has a threaded mounting stud disposed in the end wall aperture and is supported in interior of the cylinder in spaced non-contacting relation thereto. The stud extends outwardly of the other end of the sleeve and removably supports a working tip. Power supply conductors extend through the handle and sleeve and are connected to the anode of the diode within the cylinder and to the cathode of the diode through the cylinder, end wall and mounting stud. The arrangement minimizes undesirable transfer of heat from the diode to the cylinder and sleeve and maximizes transfer of heat through the threaded stud to the tip.

3 Claims, 3 Drawing Figures

FORWARD BIASED DIODE

ELECTRICALLY HEATED WAX SPATULA USING A DIODE AS THE HEATING ELEMENT

The present invention relates to wax spatulas and, more particularly, to heated wax spatulas.

As reflected by U.S. Pat. No. 2,213,438, the use of a resistive element to generate heat and transfer of that heat to a threadedly engaged tip is well known in the soldering iron art. The use of a resistive heating element to heat an attached spatula of a dental wax spatula is taught in U.S. Pat. No. 2,468,818. Similarly, U.S. Pat. Nos. 3,800,122, 3,821,513 and 3,902,043 disclose various embodiments of heated wax spatulas which employ a resistive element as a heat source for an attachable spatula or as the spatula itself. In the surgical field, U.S. Pat. No. 4,089,336 describes a cutting instrument employing a resistive element as a heated cutting edge.

Various control circuits have been developed for maintaining or adjusting the temperatures of various hand held tools having heating elements, such as soldering irons. The following United States Patents illustrate and describe representative ones of such circuits: Nos. 3,943,326, 4074,110, 4086,466 and 4,121,092. It may be noted that each of these circuits employs one or more diodes as operative elements of the circuit.

The fact that diodes, when electrically energized, generate heat is well known. Most inventions pertinent to heated diodes are directed to various heat sinks for dissipating or otherwise preventing heat buildup, as noted in U.S. Pat. Nos. 3,010,057, 3,053,032, 3,059,157 and 3,064,179.

In the field of dental work, whether performed by dentists, dental technicians, or skilled craftsmen in dental laboratories, wax impressions are made. Such wax impressions are usually worked with wax spatulas or spatula-like hand held tools which may be made of fibrous, metallic or man-made materials. As illustrated in several of the above-identified patents, heated wax spatulas are also employed to facilitate working of the wax impressions. These heated wax spatulas employ a resistive element which is heated by passing an electrical current therethrough and the heat is ultimately transferred to the working tip. The number of components necessary for such a wax spatula render the instrument operative but not optimized to the extent possible from the standpoint of cost, size, temperature control and manipulative ease.

To overcome the various problems attendant prior art spatulas, the present invention incorporates a forward biased diode as a source of heat for heating a threadedly attached working tip. Attachment of the diode to the handle of the spatula is effected through a sleeve, which sleeve mechanically supports the diode and provides structural support to the tip via the diode.

It is therefore a primary object of the present invention to provide a heated wax spatula employing an electrically energizable diode for supporting and heating the working tip.

Another object of the present invention is to provide a diode as the heating element in a hand-held heated spatula.

Yet another object of the present invention is to provide a wax spatula having a commercially availabe diode threadedly supporting the working tip.

Yet another object of the present invention is to provide a diode heated wax spatula.

A further object of the present invention is to provide a heated wax spatula having a diode as the heat generating element and an electrical control system for varying the temperature of the diode.

A still further object of the present invention is to provide a low parts count heated wax spatula.

A yet further object of the present invention is to provide a lightweight and inexpensive heated wax spatula.

These and other objects of the present invention will become apparent to those skilled in the art as the description thereof proceeds.

The present invention may be described with greater specificity and clarity with reference to the following drawings, in which.

Figure 1:
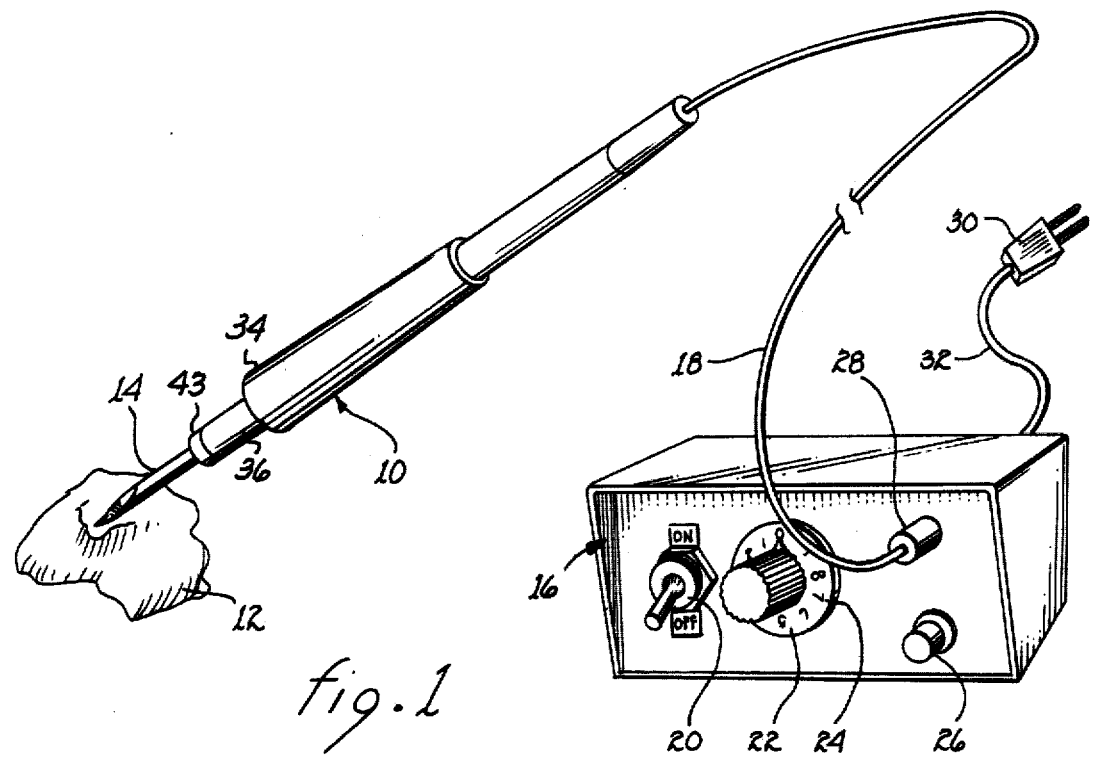
FIG. 1 illustrates a heated wax spatula and a temperature control unit therefor.

Referring to FIG. 1, there is shown a heated wax spatula 10 for working a piece of wax, respesentatively identified by numeral 12. The spatula includes an internally mounted semiconductor means, such as diode, for supplying heat by conduction to working tip 14. Direct current power for the diode is provided by control unit 16 through electrical cord 18. The control unit may include an on/off switch 20, a knob 22 having indicia 24 disposed thereon for regulating the power supplied the diode and thereby its temperature and a fuse 26. Electrical cord 18 may include a jack 28 for engagement with a socket disposed in control unit 16. Power for the control unit is provided by a conventional electrical plug 30 attached to an electrical conductor 32.

Stud mount diodes of the type suitable for use in the present invention are commercially available with diameters of ¼ of an inch or less. Hence, the supporting body of the spatula may be near pencil thin to render it easily manipulatable and useable in tight quarters. The small cross-sectional size of the diode permits the spatula to be built from the lightweight materials, and the mass of the spatula is primarily a function of cross-sectional size and length dictated by manipulation requirements rather than by operational parameters.

Figure 2:
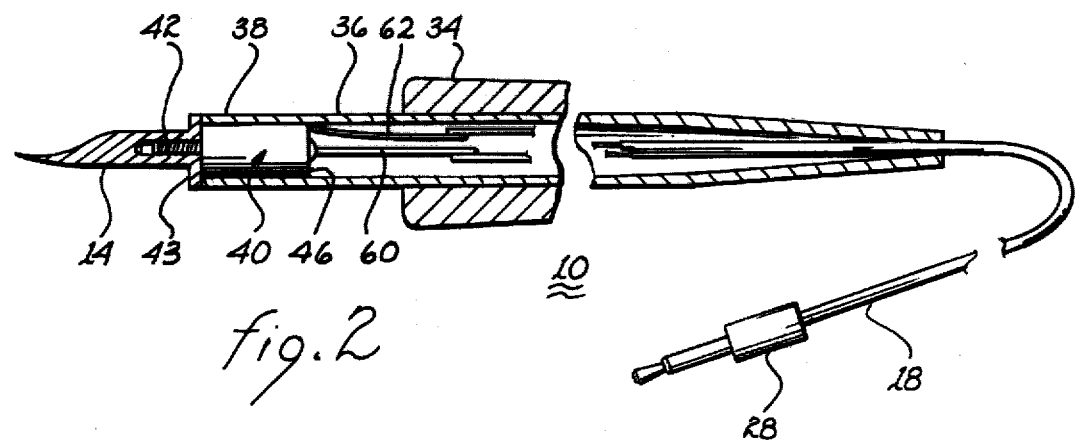
FIG. 2 is a partial cross-sectional view of the heated wax spatula.
Figure 3:
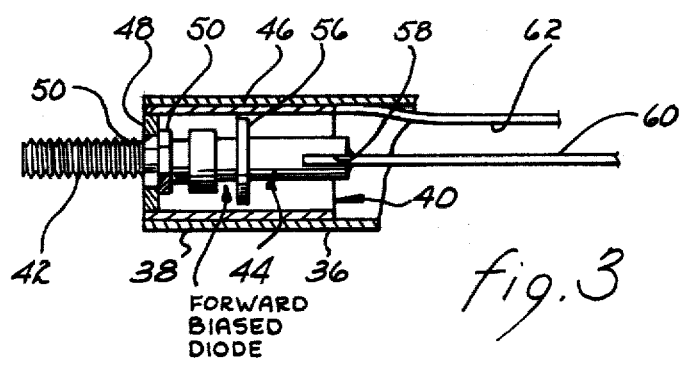
FIG. 3 is a sectional view of the operative elements of the heated wax spatula.

Turning now to FIGS. 2 and 3, various constructional details of wax spatula 10 will be described. A grip 34 encircles sleeve 36. The grip serves primarily as a surface for grasping and holding the spatula and may be of whatever diameter and external configuration found to be most suitable for the operator and the work to be performed. That is, the grip may be configured on the basis of human factors engineering. End 38 of the sleeve supports internally mounted diode unit 40. This unit may be friction fitted or attached by adhesive or other means to the internal surface of sleeve 36. The positioning of diode unit 40 extends threaded shank 42 beyond end 38. Tip 14, having an internally threaded cavity, threadedly engages with shank 42 to secure the tip of sleeve 36. An annular flange 43 extends about the base of tip 14, which flange serves two functions. First, it has the effect of sealing end 38 of sleeve 36 to prevent the ingress of contaminate matter, wax, etc. Second, it serves as a shelf to restrain the flow of wax toward the sleeve, should the spatula be held tip up.

The constructional details of diode unit 40 will be reviewed with reference to FIG. 3. A stud mount diode 44, which may be of the type known as UZ7815 and manufactured by the Unitrode Corporation of Watertown, Massachusetts, includes an annular insulator 54 intermediate integral nut 50 and an integrally formed annular flange 56. The end of the diode opposite threaded shank 42 includes a slot 58 and, by convention, is the anode of the diode. The cathode of the diode, segregated by insulator 54, includes nut 50 and threaded shank 42. The diode is secured inside a cylinder 46 having an apertured end plate 48 by soldering, brazing or otherwise attaching an element of the diode, such as integrally formed nut 50, to the end plate. Aperture 52 within the end plate is configured to accommodate passage therethrough of threaded shank 42 of the diode.

By maintaining diode 44 centrally located within cylinder 46, no contact therebetween will exist except via end plate 48. Such physical separation provides 3 benefits. First, heat transfer from diode 44 to cylinder 46 and hence to encircling sleeve 38 is minimized and localized to a point proximate the very end of the sleeve. Second, the cathode of the diode is grounded to the sleeve. Third, electrical insulation between the anode of the diode and the sleeve is maintained.

Perforce, the external constructional details of diode 44 will vary, depending upon the manufacturer, current rating and other parameters. Modifications for attaching other types of stud mount diodes can be effected commensurate with the teachings contained above.

Power to diode 44 is supplied through the electrical conductors of cord 18 to electrical conductor 60 soldered or otherwise secured to slot 58 and to electrical conductor 62 soldered or otherwise electrically secured to cylinder 46.

In operation, by activating control unit 16, electrical power is supplied to forward bias diode 44. On energization of the diode, it will heat commensurate with the setting of knob 22. Heat from the diode will be transferred to tip 14 via stud 42. The degree of temperature rise of the tip is dependent upon the power supplied to the diode commensurate with the electrical parameters of the diode. Thereby, it will be readily appreciated that the temperature of the tip can be relatively accurately controlled for working wax of any of several different chemical and physical properties.

Because of the small sized diodes which are suitable and the low parts count, the physical size of wax spatula 10 may be dictated solely by human factor considerations commensurate with the degree of intricacy of the work to be performed. Additionally, the low parts count inherently makes the wax spatula relatively inexpensive to manufacture and maintain.

As the only limitation on the temperature of tip 14 is that of the heat generatable by the diode, it may be readily understood by an appropriate selection of the diode, tip 14 may be used for soldering purposes or other functions where temperatures substantially higher than the melting point of wax are required.

As is well known to those skilled in the art, it is preferable that tip 14 be of beryllium copper or other material which will not readily oxidize or corrode.

It is to be understood that as tip 14 can be readily replaced by simply unthreading it from stud 42, variously configured and sized tips can be used in conjunction with a single sized wax spatula body.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. An electrically heated spatula for working temperature sensitive material, said spatula being connectable to a source of electrical power, said spatula comprising in combination:
   (a) a handle, a hollow sleeve extending from said handle and secured thereto at one end;
   (b) a diode unit supported within the other end of said sleeve, said diode unit comprising in combination:
      i. a diode electrically adapted to be connected to the source of electrical power for generating heat in response to the received electrical power, said diode including a stud extending therefrom;
      ii. apertured metallic plate means penetrably receiving said stud to effect a mounting for said diode; and
      iii. a metallic cylinder affixed to said plate means and extending therefrom to shroud said diode in a non-contacting relationship to minimize heat transfer by conduction from said diode to other than said stud, said cylinder being mountable within said other end of said sleeve with said stud extending outwardly from the end of said sleeve, said plate means and said cylinder being electrically conductive, and electrically connected; and
      iv. said diode including an anode terminal disposed interior of said cylinder;
      v. said diode including a cathode terminal electrically connected to said stud;
   (c) a tip for applying heat to the temperature sensitive material, said tip being removably mounted upon said stud for receiving heat from said diode through said stud; and
   (d) first and second conductors extending from the source of electrical power, said first conductor being electrically connected to said anode terminal and said second conductor being electrically connected to said cylinder.

2. The spatula as set forth in claim 1 wherein said stud is a threaded shank for threadedly engaging a threaded cavity within said tip.

3. The spatula as set forth in claim 2 wherein said tip includes an annular flange positionable adjacent said plate means on threaded engagement of said tip with said stud to maximize heat transfer from said diode unit to said tip.

* * * * *